US010557751B2

(12) United States Patent
Fujiwara et al.

(10) Patent No.: US 10,557,751 B2
(45) Date of Patent: Feb. 11, 2020

(54) METHOD, PROGRAM, CUMULATIVE RECEIVED-LIGHT AMOUNT ESTIMATION APPARATUS, AND HEALTH CARE SYSTEM USING SOLAR RADIATION AMOUNT INFORMATION CORRESPONDING TO POSITION INFORMATION OF A DEVICE AND TIME INFORMATION

(71) Applicant: Panasonic Intellectual Property Management Co., Ltd., Osaka (JP)

(72) Inventors: Yuri Fujiwara, Osaka (JP); Hiroki Noguchi, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 81 days.

(21) Appl. No.: 16/017,392

(22) Filed: Jun. 25, 2018

(65) Prior Publication Data

US 2019/0003881 A1   Jan. 3, 2019

(30) Foreign Application Priority Data

Jun. 29, 2017 (JP) .................................. 2017-127321

(51) Int. Cl.
*G01J 1/42* (2006.01)
*A61B 5/08* (2006.01)
(Continued)

(52) U.S. Cl.
CPC .................. *G01J 1/42* (2013.01); *A61B 5/08* (2013.01); *A61B 5/0823* (2013.01);
(Continued)

(58) Field of Classification Search
CPC ......... A61B 5/01; A61B 5/024; A61B 5/0533; A61B 5/7275; G01J 1/42; G01N 7/14; G16H 20/40; G16H 40/60
(Continued)

(56) References Cited

U.S. PATENT DOCUMENTS 7,166,825 B1 * 1/2007 Smith ...................... G01J 1/02
250/203.4
2017/0065827 A1 3/2017 Fujiwara et al.

FOREIGN PATENT DOCUMENTS

JP   02-115726 A   4/1990
JP   2009-238652 A   10/2009
(Continued)

OTHER PUBLICATIONS

Honma, Kenichi, et al., "Biological Rhythms", Hokkaido University Press, pp. 264-273, 1989 with partial English translation.
(Continued)

*Primary Examiner* — Que Tan Le
(74) *Attorney, Agent, or Firm* — McDermott Will & Emery LLP

(57) ABSTRACT

A method includes: receiving, by a terminal device, position information of the terminal device via a wireless signal, and time information; obtaining solar radiation amount information corresponding to the position information of the terminal device and the time information; obtaining a corrected received-light amount by correcting the amount of light received by the terminal device, based on a radio field reception intensity of the wireless signal that includes the position information, the amount of light received being indicated in the solar radiation amount information; and obtaining, by the terminal device, a cumulative value of amounts of light which the user of the terminal device has been exposed to, using the corrected received-light amount.

20 Claims, 8 Drawing Sheets

(51) Int. Cl.
| | |
|---|---|
| *A61B 5/00* | (2006.01) |
| *G16H 40/60* | (2018.01) |
| *G01N 7/14* | (2006.01) |
| *A61B 5/024* | (2006.01) |
| *A61B 5/053* | (2006.01) |
| *A61B 5/145* | (2006.01) |
| *A61B 5/113* | (2006.01) |
| *A61B 5/01* | (2006.01) |
| *G16H 20/40* | (2018.01) |

(52) U.S. Cl.
CPC .......... *A61B 5/0826* (2013.01); *A61B 5/4818* (2013.01); *A61B 5/4857* (2013.01); *A61B 5/7275* (2013.01); *G01N 7/14* (2013.01); *G16H 40/60* (2018.01); *A61B 5/01* (2013.01); *A61B 5/024* (2013.01); *A61B 5/0533* (2013.01); *A61B 5/113* (2013.01); *A61B 5/14542* (2013.01); *A61B 5/441* (2013.01); *A61B 5/4806* (2013.01); *G01J 2001/4266* (2013.01); *G16H 20/40* (2018.01)

(58) Field of Classification Search
USPC .............................. 250/214 AL, 214.1, 203.4
See application file for complete search history.

(56) References Cited

FOREIGN PATENT DOCUMENTS

| JP | 2016-192611 A | 11/2016 |
|---|---|---|
| JP | 2017-051375 A | 3/2017 |

OTHER PUBLICATIONS

Hashimoto, Satoko, et al., "Midday exposure to bright light changes the circadian organization of plasma melatonin rhythm in humans", Neuroscience Letters, vol. 221, pp. 89-92, Jan. 1997.

Kozaki, Tomoaki, et al., "The Advancing Effect of Different Light Intensities in the Morning on Dim Light Melatonin Onset (DLMO) and Its Phase Response", Japanese Journal of Physiological Anthropology, vol. 19, No. 1, pp. 7-11, 2014.

* cited by examiner

FIG. 5

| TIME<br>(TIME INFORMATION) | PLACE<br>(POSITION INFORMATION) | ILLUMINANCE |
|---|---|---|
| 06:30 - 07:30 | LIVING ROOM AT HOME | 500 lx |
| 07:30 - 08:30 | OUTDOORS | 4000 lx |
| 08:30 - 12:00 | OFFICE | 300 lx |
| 12:00 - 13:00 | RESTAURANT | 200 lx |
| 13:00 - 18:00 | OFFICE | 300 lx |
| 18:00 - 19:00 | OUTDOORS | 100 lx |
| 19:00 - 23:00 | LIVING ROOM AT HOME | 200 lx |
| 23:00 - 06:30 | BED ROOM AT HOME | 0 lx |

METHOD, PROGRAM, CUMULATIVE RECEIVED-LIGHT AMOUNT ESTIMATION APPARATUS, AND HEALTH CARE SYSTEM USING SOLAR RADIATION AMOUNT INFORMATION CORRESPONDING TO POSITION INFORMATION OF A DEVICE AND TIME INFORMATION

CROSS REFERENCE TO RELATED APPLICATION

This application claims the benefit of priority of Japanese Patent Application Number 2017-127321 filed on Jun. 29, 2017, the entire content of which is hereby incorporated by reference.

BACKGROUND

1. Technical Field

The present disclosure relates to a method, a program, a cumulative received-light amount estimation apparatus, and a health care system.

2. Description of the Related Art

In recent years, the exposure of a body to light for the purpose of adjusting one's biological clock and regulating one's biological rhythm has been put into practice as one of the methods for correcting biological rhythm disturbance. The biological clock is adjusted by regulating the biological rhythm, and it is thus possible to awaken the body during the day.

Conventionally, a lighting control system including a biological information obtainer that obtains biological information related to the biology of a user, and an environment information obtainer that obtains environment information related to the surrounding environment of the user has been disclosed (see reference, for example, to Patent Literature 1 (PTL 1): Japanese Unexamined Patent Application Publication No. 2017-51375).

SUMMARY

In the conventional lighting control system, a user wears a sensor on the body and the sensor calculates a cumulative value of the amounts of light which the user has been exposed to. However, the user may feel inconvenient because he/she has to wear a sensor. In addition, although it is expected that, with a sensor worn on the body, the sensor is capable of precisely calculating an amount of light which the user has been exposed to, the following problems may occur in some cases. A measured amount of received light may be less than an actual amount of the received light or communication errors may occur between the sensor and a terminal device for storing data on the amount of received light, due to, for example, the sensor being blocked by cloths, hairs, etc., or missing of data may occur because of dead battery, etc. It is therefore difficult to precisely obtain an amount of received light in the conventional lighting control system.

In view of the above, the present disclosure has an object to provide a method, a program, a cumulative received-light amount estimation apparatus, and a health care system which enable, without the use of a sensor, precise estimation of a cumulative value of the amounts of light which the user has been exposed to.

In order to achieve the above-described object, a method according to one aspect of the present disclosure is a method including: receiving, by a device, position information of the device via a wireless signal, and time information; obtaining solar radiation amount information corresponding to the position information and the time information, the solar radiation amount information indicating an amount of solar radiation corresponding to the position information of the device and the time information; obtaining a corrected received-light amount by correcting the amount of solar radiation, based on a radio field reception intensity of the wireless signal that includes the position information, the amount of solar radiation being indicated by the solar radiation amount information; and obtaining, by the device, a cumulative value of amounts of light which a user of the device has been exposed to, using the corrected received-light amount.

Moreover, in order to achieve the above-described object, a non-transitory computer readable medium storing a program according to one aspect of the present disclosure causes a computer to execute the above-described method.

Moreover, in order to achieve the above-described object, a cumulative received-light amount estimation apparatus according to one aspect of the present disclosure is a cumulative received-light amount estimation apparatus including: a solar radiation amount obtainer that obtains solar radiation amount information corresponding to position information of a device and time information; a received-light amount calculator that calculates a corrected received-light amount obtained by correcting an amount of light received by the device, based on a radio field reception intensity of a signal that includes the position information, the amount of light received being indicated by the solar radiation amount information; and a cumulative value calculator that calculates a cumulative value that includes the corrected received-light amount.

Furthermore, in order to achieve the above-described object, a health care system according to one aspect of the present disclosure includes: the above-described cumulative received-light amount estimation apparatus; a managing computer that manages an amount of light which a user is exposed to, a health condition of the user, and a sleeping condition of the user, based on the cumulative value obtained from the cumulative received-light amount estimation apparatus; and a lighting apparatus.

According to the present disclosure, it is possible, even without the use of a sensor, to precisely estimate a cumulative value of the amounts of light which the user has been exposed to.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 5 is an explanatory diagram illustrating an example of the calculation of the cumulative value of the amounts of light which the user has been exposed to in one day;

DETAILED DESCRIPTION OF THE EMBODIMENTS

[Outline]

It has been known that plural factors exert a regulatory influence over a biological clock having a biological rhythm (also referred to as circadian rhythm) of a person. It has been known that "light" has the greatest influence among the physical factors included in such factors (Non-Patent Literature 1 (NPTL 1): Kenichi Honma, Sato Honma, Tsutomu Hiroshige, "Biological Rhythms" Hokkaido University Press, 1989). Basically, when the amount of light which one has been exposed to during the day is deficient, one's biological rhythm gets disturbed, and this causes various disorders such as sleeping disorder, deterioration of concentration due to sleeping disorder, etc.

In a research related to light and the secretion of melatonin known as a hormone related to biological rhythm, it is verified that exposure to light with illuminance of 5,000 lx for six hours (from 11:00 to 17:00) for a healthy male adult (Non-Patent Literature 2 (NPTL 2): S. Hashimoto, M. Kohsaka, K. Nakamura, H. Honma, S. Honma, K. Honma. "Midday exposure to bright light changes the circadian organization of plasma melatonin rhythm in humans", Neurosci. Lett., 221, 89-92 (1997)) and exposure to light with illuminance of 1,500 lx for three hours (from 09:00 to 12:00) for a healthy late-night male adult (Non-Patent Literature 3 (NPTL 3): Tomoaki Kozaki, Miyuki Ina, and Akira Yasukouchi. "The advancing effect of different light intensities in the morning on dim light melatonin onset (DLMO) and its phase response", Japan Society of Physiological Anthropology, Vol. 19, No. 1, pages 7 to 11 (2014)) each result in an increase in the amount of melatonin secretion and the advancement of the circadian phase of the melatonin secretion, and thereby, one's biological rhythm is regulated. It is said that in order for a healthy person to regulate his/her biological rhythm, exposure to light with high illuminance of approximately 1,500 lx for at least three hours during the day is necessary.

Figure 9:
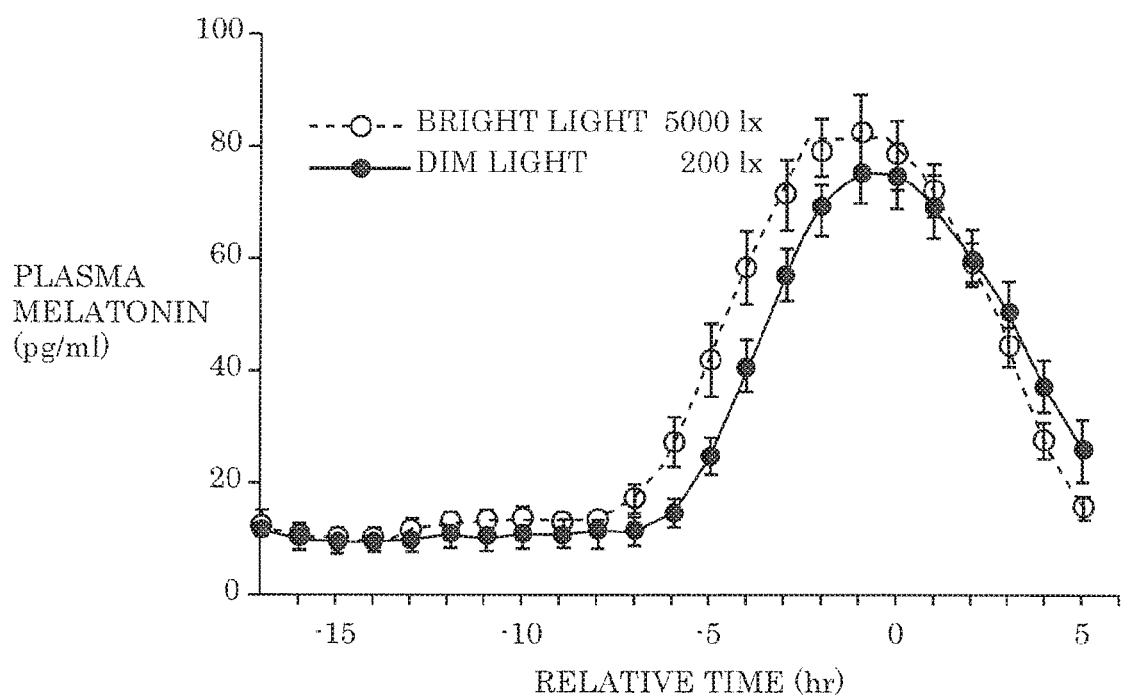
FIG. 9 is a diagram illustrating a relationship between an amount of melatonin secretion and hourly variation of the amount of melatonin secretion.

FIG. 9 is a diagram illustrating a relationship between the amount of melatonin secretion and the hourly variation of the amount of melatonin secretion. According to NPTL 2, exposure to light having illuminance of 5,000 lx for six hours during the day produces an effect of promoting melatonin secretion and advancing the circadian phase of the melatonin secretion, and thus, a biological rhythm may be regulated. According to NPTL 3, a report statistically shows that in the case of irradiating light having illuminance of 1,500 lx, 3,000 lx, or 6,000 lx, a dim light melatonin onset (DLMO) significantly advances from the next day following the day on which such light has been irradiated, and thus, a biological rhythm may be regulated.

Therefore, in order for the user to know that he/she has not sufficiently been exposed to light during the day, it is useful to calculate an amount of light which the user has been exposed to during the day, and thereby make the user realize the amount of light which he/she has been exposed to.

Hereinafter, the embodiments of the present disclosure will be described with reference to the drawings. The subsequently-described embodiments show specific examples of the present disclosure. Accordingly, the numerical values, shapes, materials, structural components, the arrangement and connection of the components, etc. shown in the following embodiments are mere examples, and are not intended to limit the scope of the present disclosure. Therefore, among the structural components in the following embodiments, components not recited in any one of the independent claims which indicate the broadest concepts of the present disclosure are described as arbitrary structural components.

Note that the respective figures are schematic diagrams and are not necessarily precise illustrations. In addition, in the respective figures, substantially identical components are assigned the same reference signs, and overlapping description is omitted or simplified.

The following describes a cumulative received-light amount estimation method (method), a program, a cumulative received-light amount estimation apparatus, and a health care system, according to an embodiment of the present disclosure.

Embodiment 1

[Configuration]

Figure 1:
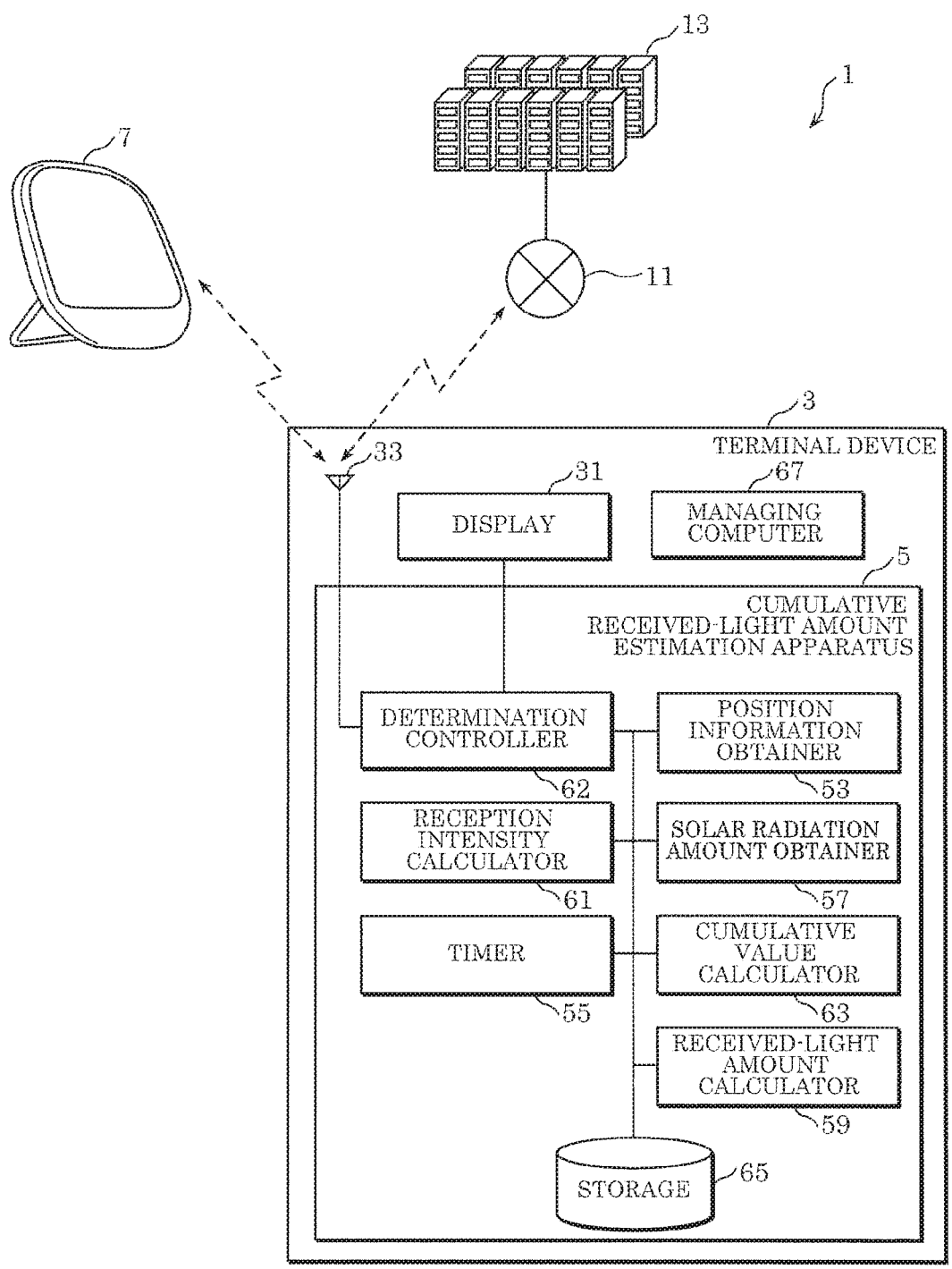
FIG. 1 is a block diagram illustrating a health care system according to Embodiment 1.

FIG. 1 is a block diagram illustrating health care system 1 according to Embodiment 1.

As illustrated in FIG. 1, health care system 1 is a system for calculating a cumulative value obtained, for example, by adding amounts of light received by terminal device 3 during one day, and managing the light output of lighting apparatus 7 etc., based on the calculated cumulative value. Health care system 1 includes terminal device 3 and lighting apparatus 7. Light output signifies brightness.

Terminal device 3 is, for example, a device such as a smart phone or a tablet terminal. Terminal device 3 is normally assumed to be carried by the user of terminal device 3, and an amount of received-light calculated by terminal device 3, that is, an amount of light received by terminal device 3, is regarded as an amount of light which the user has been exposed to. The amount of received light described in this embodiment is calculated by multiplying the brightness of light by a light receiving period. Terminal device 3 is an example of a device.

Terminal device 3 includes cumulative received-light amount estimation apparatus 5, managing computer 67, display 31, and terminal communication unit 33.

Cumulative received-light amount estimation apparatus 5 is an apparatus that estimates an amount of light which the user has been exposed to, based on position information of terminal device 3, time information, etc. Cumulative received-light amount estimation apparatus 5 includes position information obtainer 53, timer 55, solar radiation amount obtainer 57, received-light amount calculator 59, reception intensity calculator 61, determination controller 62, cumulative value calculator 63, and storage 65.

Position information obtainer 53 obtains the position information of terminal device 3 using GPS (Global Positioning System). The position information obtained by position information obtainer 53 indicates a current position of terminal device 3. Position information obtainer 53 outputs the obtained position information to solar radiation amount obtainer 57, etc.

Timer 55 measures a current time and outputs the measured current time to determination controller 62, solar radiation amount obtainer 57, etc. Timer 55 outputs, for example, time information per unit time, to determination controller 62, solar radiation amount obtainer 57, etc. Accordingly, determination controller 62 is capable of determining whether or not the current time is within a target time period. More specifically, timer 55 may be a general timer circuit.

Solar radiation amount obtainer 57 obtains the position information of terminal device 3 from position information obtainer 53, and obtains time information corresponding to the position information, from timer 55. Solar radiation amount obtainer 57 associates the obtained position information of terminal device 3 with the obtained time information. Note that in the case where position information has already been associated with time information, that is, the case where position information obtainer 53 obtains information in which position information and time information are associated with each other, solar radiation amount obtainer 57 need not associate position information with time information.

Solar radiation amount obtainer 57 obtains, from external server 13 via terminal communication unit 33 and network 11, solar radiation amount information corresponding to the obtained position information and time information. Solar radiation amount obtainer 57 outputs the obtained solar radiation amount information to received-light amount calculator 59. The solar radiation amount information indicates an amount of solar radiation received by terminal device 3. Server 13 described in this embodiment is a server provided at a meteorological institute or the like, and solar radiation amount obtainer 57 obtains solar radiation amount information from information officially announced by a meteorological institute or the like.

Reception intensity calculator 61 calculates a current radio field reception intensity, which is the intensity of radio field currently being received by terminal communication unit 33 of terminal device 3. Reception intensity calculator 61 outputs information indicating the calculated radio field reception intensity to determination controller 62, etc.

Received-light amount calculator 59 calculates a corrected received-light amount by correcting an amount of solar radiation indicated by the solar radiation amount information, based on the radio field reception intensity of a wireless signal that includes position information. More specifically, when determination controller 62 determines that the radio field reception intensity is higher than or equal to the first threshold value and is lower than the second threshold value, received-light amount calculator 59 calculates the first corrected received-light amount obtained by correcting an amount of light received by terminal device 3, using the first correction coefficient derived with use of the first correction coefficient function. When determination controller 62 determines that the radio field reception intensity is higher than or equal to the second threshold value, received-light amount calculator 59 calculates the second corrected received-light amount by correcting an amount of light received by terminal device 3, using the second correction coefficient derived with use of the first correction coefficient function. Stated differently, the corrected received-light amount includes the first corrected received-light amount and the second corrected received-light amount. Received-light amount calculator 59 outputs the calculated first corrected received-light amount and second corrected received-light amount to cumulative value calculator 63.

Figure 2:
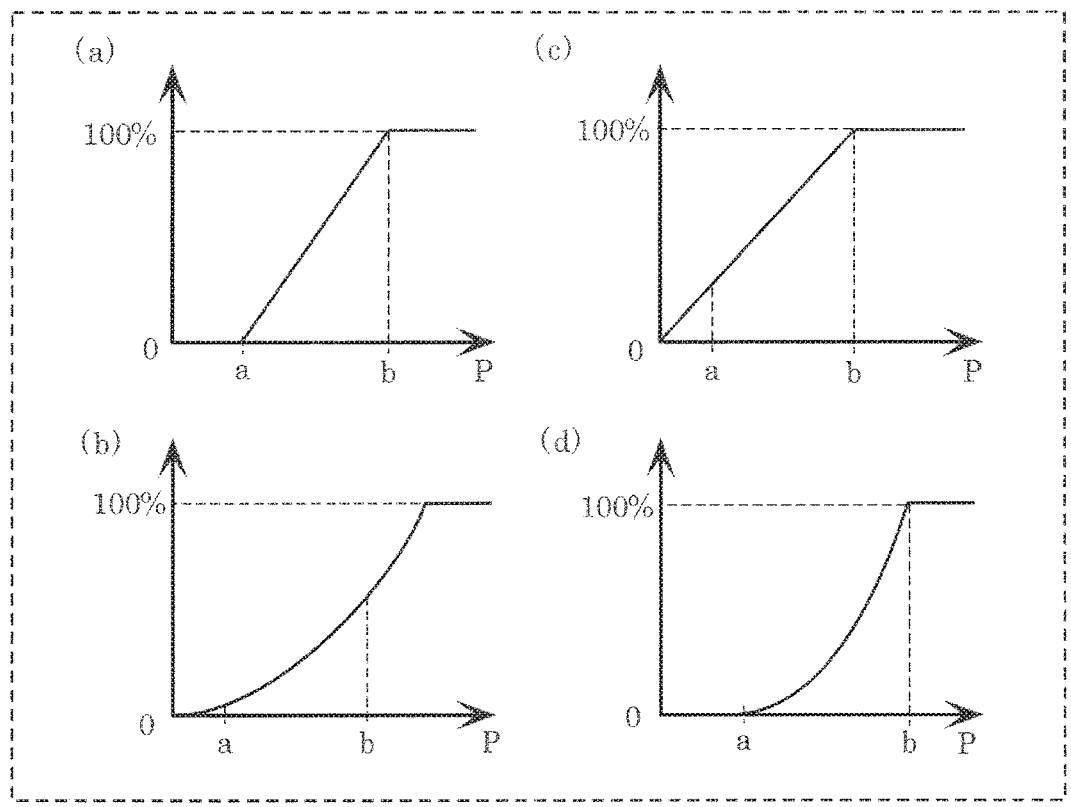
FIG. 2 is a diagram illustrating examples of the first correction coefficient function to be used by a cumulative received-light amount estimation apparatus according to Embodiment 1.

The first correction coefficient function is, for example, a non-decreasing function, and is illustrated, for example, in FIG. 2. FIG. 2 is a diagram illustrating the examples of the first correction coefficient function to be used by cumulative received-light amount estimation apparatus 5 according to Embodiment 1. A line represented in the first correction coefficient function may be curved, straight, or stepwise, or may be an arbitrary combination of these. In FIG. 2, a vertical axis represents a correction coefficient while a horizontal axis represents radio field reception intensity P. First correction coefficient k1 and second correction coefficient k2 are calculated based on this first correction coefficient function.

Referring to (a) in FIG. 2 as an example, when radio field reception intensity P is lower than first threshold value a, correction coefficient k0 becomes 0%. That is to say, k0=0. Moreover, when radio field reception intensity P is higher than or equal to first threshold value a and is lower than second threshold value b, first correction coefficient k1 is derived based on a range of from first threshold value a to second threshold value b, and this results in 0<k1<1. Furthermore, when radio field reception intensity P is higher than or equal to second threshold value b, second correction coefficient k2 becomes 100%. That is to say, k2=1.

When radio field reception intensity P is lower than first threshold value a, the radio field intensity of terminal device 3 is weak, and therefore, it is likely that the user is indoors where the sunlight hardly comes in. Accordingly, when the radio field reception intensity is lower than first threshold value a, it is likely that almost no sunlight is received, and therefore, the value of correction coefficient k0 shall be 0 or a value approximated to 0.

Moreover, when radio field reception intensity P is higher than or equal to first threshold value a and is lower than second threshold value b, the radio field intensity of terminal device 3 is moderate and it is likely that the user is either indoors, e.g., near a window that lets the sunlight in, or outdoors, e.g., under the shade of a tree. Second threshold value b is a value greater than first threshold value a. Thus, when radio field reception intensity P is higher than or equal to first threshold value a and is lower than second threshold value b, the radio field intensity is moderate, and it is likely that terminal device 3 more or less receives the sunlight. Therefore, the value of first correction coefficient k1 shall be a value greater than correction coefficient k0.

Furthermore, when radio field reception intensity P is higher than or equal to second threshold value b, the radio field intensity of terminal device 3 is high and it is likely that the user is outdoors where he/she is exposed directly to the sunlight. Thus, when radio field reception intensity P is higher than or equal to second threshold value b, the radio field intensity is high, and it is likely that terminal device 3 receives the sunlight. Therefore, the value of second correction coefficient k2 shall be a value greater than correction coefficient k0 and first correction coefficient k1, and shall be 1 or a value approximated to 1. Note that all of correction coefficient k0, first correction coefficient k1, and second correction coefficient k2 indicate 0 or greater.

As illustrated in FIG. 1, received-light amount calculator 59 calculates a received lighting-apparatus light amount.

More specifically, light receiving period information indicating a light receiving period during which terminal device 3 has received light emitted by lighting apparatus 7, and information indicating an amount of light which terminal device 3 has received from lighting apparatus 7, the received lighting-apparatus light amount is calculated by multiplying a light receiving period by an amount of light which terminal device 3 has received from lighting apparatus 7. Received-light amount calculator 59 outputs information indicating received lighting-apparatus light amount to cumulative value calculator 63.

Determination controller 62 performs various types of determinations and control based on the determinations, for calculating, by terminal device 3, a cumulative value of the amounts of light which the user of terminal device 3 has been exposed to. Thus, determination controller 62 determines whether or not a current time is within a target time period for adding an amount of received light. To be more specific, determination controller 62 obtains information indicating a current time, from timer 55, and determines whether or not the current time is within the target time period. The target time period described in this embodiment refers to a time zone in which exposure to light produces an effect of regulating a human biological rhythm. It has been known that exposure to light having brightness of approximately 1,500 lx for about three hours during a period starting from a time when the sun starts to rise or a time one wakes up until four o'clock in the afternoon corrects one's biological rhythm, e.g., regulates one's biological rhythm.

In the case of determining that the current time is within the target time period, determination controller 62 determines whether or not a radio field reception intensity is higher than or equal to the first threshold value and is lower than the second threshold value. More specifically, determination controller 62 obtains a current radio field reception intensity of terminal device 3 from reception intensity calculator 61, and determines whether or not the current radio field reception intensity is higher than or equal to the first threshold value and is lower than the second threshold value. Here, the first threshold value is a value smaller than the second threshold value.

In the case of determining that the radio field reception intensity is lower than the first threshold value, determination controller 62 determines whether or not the user is using lighting apparatus 7. Determination controller 62 is capable of determining that the user is using lighting apparatus 7 when determination controller 62 is able to obtain, from lighting apparatus 7 via terminal communication unit 33, information indicating the brightness of lighting apparatus 7.

When the user is using lighting apparatus 7, determination controller 62 obtains information indicating the brightness of lighting apparatus 7. The information indicating the brightness of lighting apparatus 7 indicates the light output of light emitted by lighting apparatus 7, and indicates an amount of light which is emitted by lighting apparatus 7 and received by terminal device 3. In addition, determination controller 62 obtains time information from timer 55 while obtaining the information indicating brightness, and generates light receiving period information. Determination controller 62 associates, with the light receiving period information, the information indicating the brightness of the light which is emitted by lighting apparatus 7 and received by terminal device 3, and outputs the associated information to received-light amount calculator 59.

Determination controller 62 also determines whether or not the brightness of the light emitted by lighting apparatus 7 is higher than or equal to a predetermined value. Stated differently, determination controller 62 determines whether a time period during which terminal device 3 has received the light emitted by lighting apparatus 7 includes a time period during which the brightness of the light emitted by lighting apparatus 7 is higher than or equal to a predetermined value. This determination is made to exclude an amount of light which is emitted by lighting apparatus 7 and has brightness lower than the predetermined value since the effect of correcting a biological rhythm cannot be expected when the brightness of light is low. Thus, determination controller 62 excludes, from a cumulative value to be calculated by cumulative value calculator 63, an amount of light received in a time period during which the brightness of the light emitted by lighting apparatus 7 is lower than the predetermined value.

Figure 3:
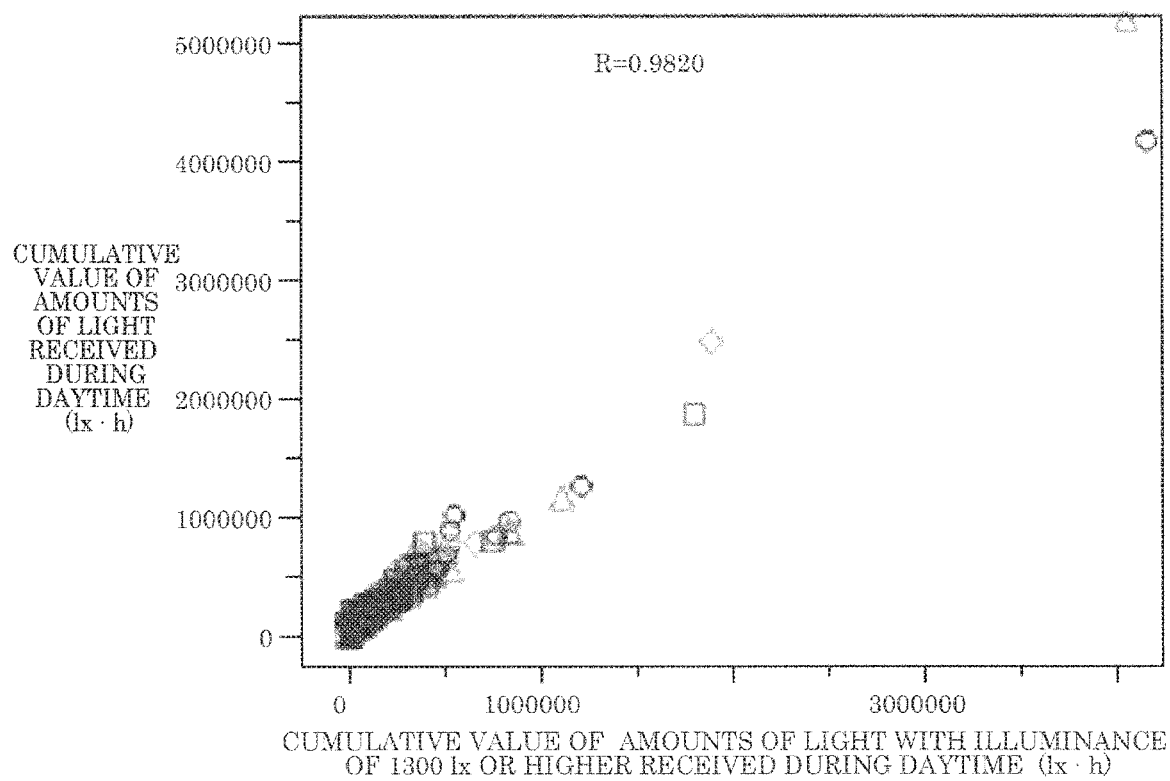
FIG. 3 is a scatter diagram illustrating a relationship between a cumulative value of the amounts of light received during daytime and a cumulative value of the amounts of light having illuminance of 1300 lx or higher received during daytime.

Here, the case of excluding, from a cumulative value, an amount of received light that is smaller than a predetermined value will be described using an example. FIG. 3 is a scatter diagram indicating a relationship between a cumulative value of the amounts of light received during day time and a cumulative value of the amounts of light with illuminance of 1,300 lx or higher received during daytime.

FIG. 3 illustrates the amounts of light received by 5 persons for 427 days in total from July to December 2016. In FIG. 3, a vertical axis represents a cumulative value (lx·h) of the amounts of light received during daytime (from wake-up time until 16:00) while a horizontal axis represents a cumulative value (lx·h) of the amounts of light with illuminance of 1,300 lx or higher received during daytime. The cumulative value of the amounts of received light with illuminance of 1,300 lx or higher, here, refers to a cumulative value obtained by adding only the amounts of received light with illuminance of 1,300 lx or higher. For this reason, an amount of light with low illuminance that is lower than 1,300 lx is excluded from the cumulative value, in FIG. 3. A predetermined value for illuminance is 1,300 lx.

The scatter diagram in FIG. 3 shows cumulative values of amounts of received light calculated by measuring illuminance every second. The case where a calculated cumulative value exceeded 1,000 lx is the case where a person was exposed to sunlight or used lighting apparatus 7 that emits light with high illuminance, and a calculated cumulative value did not exceed 1,000 lx in the case where a person was present in a general illuminated environment.

The cumulative values represented by the vertical axis and the cumulative values represented by the horizontal axis have a statistically-significant strong correlation R expressed as R=0.9820. Therefore, while the amount of received light with low illuminance that is lower than 1,300 lx is excluded from a cumulative value, it is possible to estimate the cumulative value during daytime based only on the amounts of received light with high illuminance that is 1,300 lx or higher.

As illustrated in FIG. 1, cumulative value calculator 63 calculates a cumulative value of the amounts of light which the user of terminal device 3 has been exposed to, using corrected received-light amounts. More specifically, cumulative value calculator 63 obtains, from received-light amount calculator 59, information indicating the first corrected received-light amount and the second corrected received-light amount, and calculates a cumulative value by adding the received lighting-apparatus light amount, the first corrected received-light amount, and the second corrected received-light amount.

In the calculation of a cumulative value, when the brightness of the light emitted by lighting apparatus 7 is lower than a predetermined value, cumulative value calculator 63 calculates a cumulative value without adding a received lighting-apparatus light amount to a corrected received-light amount. When the brightness of the light emitted by lighting apparatus 7 is higher than or equal to the predetermined value, cumulative value calculator 63 calculates a cumulative value by adding a received lighting-apparatus light amount to a corrected received-light amount. Cumulative value calculator 63 outputs the calculated cumulative value to determination controller 62, managing computer 67, etc. Determination controller 62 obtains the cumulative value calculated by cumulative value calculator 63, and causes display 31 to display the cumulative value. This enables the user to know the cumulative value.

In addition, determination controller 62 calculates a received-light amount in accordance with the activity of the user based, for example, on activity information of the user which is based on schedule information of one day, one week, one month, etc., of the user. The schedule information indicates, for example, a daily schedule of the user, such as a commutation to and from work, meetings, and outings. Determination controller 62 generates schedule information and causes storage 65 to store the generated schedule information. Determination controller 62 calculates solar radiation amount information corresponding to scheduled position information and scheduled time information that are associated with the schedule information, and causes storage 65 to store the calculated solar radiation amount information.

Storage 65 is a storage device that includes a memory and so on, and stores a control program etc. executed by determination controller 62. Storage 65 stores the schedule information of the user, and the scheduled position information and the scheduled time information that are associated with the schedule information. Storage 65 also stores a target time period, the first threshold value, the second threshold value, a predetermined value, a cumulative value, etc.

Managing computer 67 of terminal device 3 obtains a cumulative value from cumulative value calculator 63. Managing computer 67 manages an amount of light which the user is exposed to, a sleeping condition of the user, and a health condition of the user, based on the cumulative value obtained from cumulative received-light amount estimation apparatus 5. Managing computer 67 controls at least one of brightness of light emitted by lighting apparatus 7 and a light emitting period of lighting apparatus 7, based on the amount of light which the user is exposed to, on information indicating the health condition of the user, and on information indicating the sleeping condition of the user. Light emitting period is a time period during which light apparatus 7 emits light.

For example, when an amount of light the user has been exposed to in one day is less than an amount of received light which the user is recommended to be exposed to in one day (e.g., a value that is previously set), managing computer 67 controls lighting apparatus 7 from the following day, for example, by increasing a light output which is the brightness of lighting apparatus 7 or increasing the length of the light emitting period of lighting apparatus 7 (i.e., extending the light emitting period of lighting apparatus 7). When the amount of light the user is exposed to in one day is more than or equal to an amount of light which the user is recommended to be exposed to in one day, managing computer 67 controls lighting apparatus 7, for example, by decreasing the light output of lighting apparatus 7 or shortening the light emitting period of lighting apparatus 7 to an extent that the amount of light the user is exposed to does not go below the recommended amount. Note that when the amount of light the user has been exposed to in one day is little, managing computer 67 may cause display 31 to display that the amount of light he/she has been exposed to is insufficient.

Moreover, managing computer 67 may not be included in terminal device 3 and may be included in server 13 or another device different from terminal device 3 and server 13. Alternatively, managing computer 67 may be included in cumulative received-light amount estimation apparatus 5.

Display 31 of terminal device 3 is, for example, a liquid crystal display or an organic EL panel, and has a function to display information such as a cumulative value of the amounts of light the user has been exposed to in one day.

Terminal communication unit 33 of terminal device 3 is an antenna that obtains solar radiation amount information from server 13, position information, etc. Terminal device 3 transmits, to lighting apparatus 7, a command for controlling the brightness and the light emitting period of lighting apparatus 7.

Lighting apparatus 7 of health care system 1 shall not be limited to a device, such as a ceiling light and a pendant light, which illuminates the surrounding area, and may be, for example, a light-irradiating apparatus which irradiates the user with light. FIG. 1 of the present embodiment illustrates a light-irradiating apparatus as an example of lighting apparatus 7.

[Operation]

The following describes an operation of cumulative received-light amount estimation apparatus 5.

Figure 4:
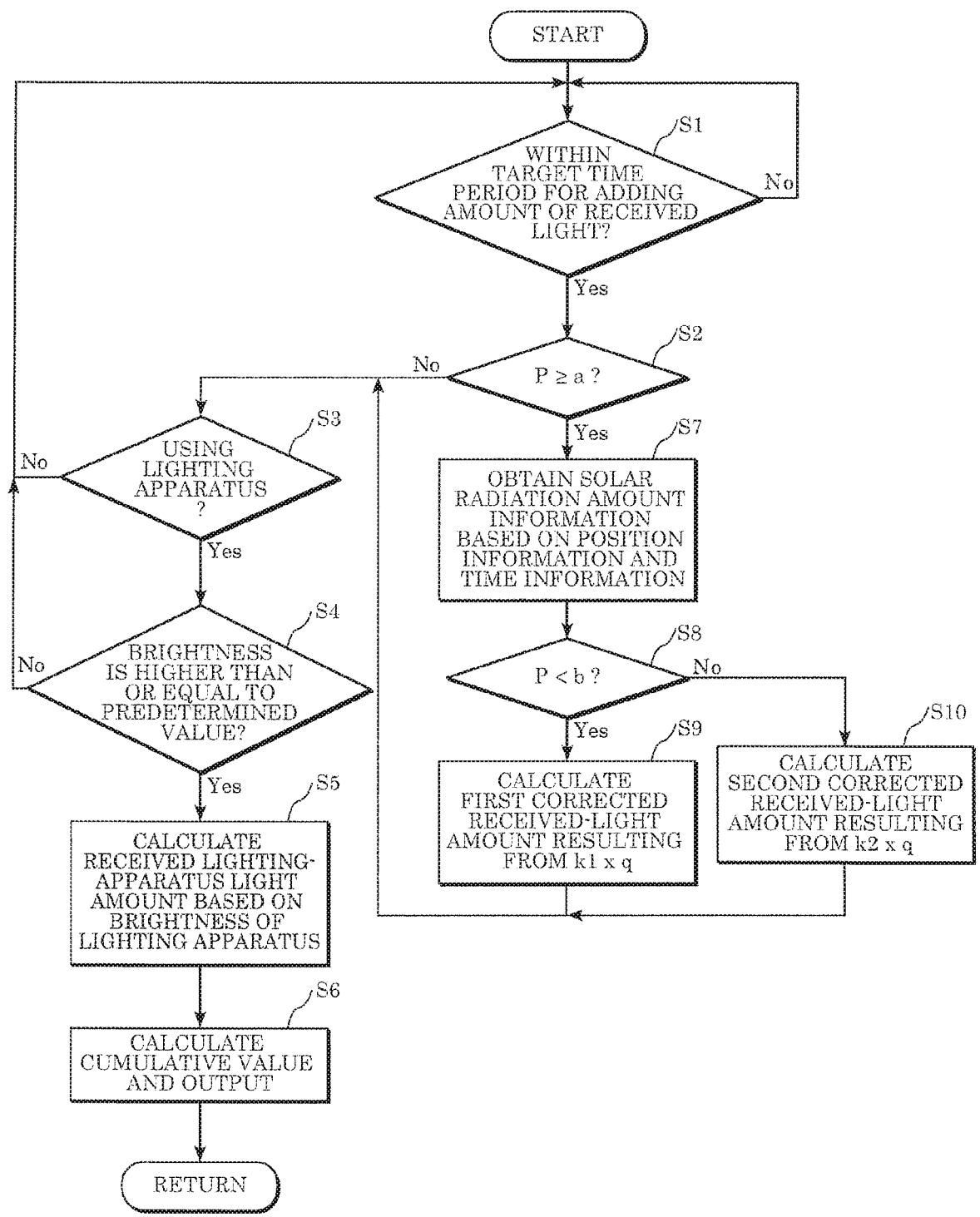
FIG. 4 is a flowchart illustrating the operation performed by the cumulative received-light amount estimation apparatus according to Embodiment 1.

FIG. 4 is a flowchart illustrating the operation of cumulative received-light amount estimating apparatus 5 according to Embodiment 1.

The user starts up an application exclusively intended for calculating a cumulative value of the amounts of light received by terminal device 3. With this, the user calculates a cumulative value of the amounts of light the user has been exposed to.

As illustrated in FIG. 4, determination controller 62 firstly determines whether or not a current time is within a target time period for adding an amount of received light (S1). In order to calculate an amount of light terminal device 3 has received during a target time period effective for correcting a biological rhythm, determination controller 62 determines whether or not a current time is within the target time period.

In the case of determining that the current time is not within the target time period (No in S1), determination controller 62 returns to step S1 and carries out the same process for determination.

On the contrary, in the case of determining that the current time is within the target time period (Yes in S1), determination controller 62 determines whether or not radio field reception intensity P is higher than or equal to first threshold value a (S2).

In the case of determining that radio field reception intensity P is lower than first threshold value a (No in S2), determination controller 62 determines whether or not the user is using lighting apparatus 7 (S3).

Note that in the case where radio field reception intensity P is lower than first threshold value a, solar radiation amount obtainer 57 may obtain solar radiation amount information based on position information and time information, but this step is omitted because an amount of solar radiation is multiplied by correction coefficient k0 and this results in an amount of solar radiation indicating 0 or a value approximated to 0. Note also that such a step may be inserted between step S2 and step S3.

In the case of determining that the user is not using lighting apparatus 7 (No in S3), determination controller 62 returns to step S1 and carries out the same process for determination.

On the contrary, in the case of determining that the user is using lighting apparatus 7 (Yes in S3), determination controller 62 determines whether or not the brightness of light emitted by lighting apparatus 7 is higher than or equal to a predetermined value (S4).

In the case of determining that the brightness of the light emitted by lighting apparatus 7 is lower than the predetermined value (No in S4), determination controller 62 returns to step S1 and carries out the same process for determination. The case of No in step S4 is the case where the brightness of the light emitted by lighting apparatus 7 is lower than the predetermined value in all of the time periods during which the user has been exposed to the light emitted by lighting apparatus 7. It is conceivable that the user is not exposed to light that is effective for correcting his/her biological rhythm during the target time period, and therefore, the amount of received light calculated during that period shall not be included in a cumulative value.

On the contrary, in the case of determining that the brightness of the light emitted by lighting apparatus 7 is higher than or equal to the predetermined value (Yes in S4), determination controller 62 calculates, based on the brightness of the light emitted by lighting apparatus 7, received lighting-apparatus light amount in the time period during which terminal device 3 has received the light emitted by lighting apparatus 7 (S5). The case of Yes in step S4 is the case where a time period during which the brightness of the light emitted by lighting apparatus 7 is higher than or equal to the predetermined value exists. Determination controller 62 therefore calculates received lighting-apparatus light amount in the time period during which the brightness of the light emitted by lighting apparatus 7 is higher than or equal to the predetermined value, excluding the time period during which the brightness of the light emitted by lighting apparatus 7 is lower than the predetermined value (S5).

Next, cumulative value calculator 63 calculates a cumulative value by adding a received lighting-apparatus light amount to a corrected received-light amount (S6). Then, determination controller 62 outputs the calculated cumulative value to display 31 (S6). With this, display 31 displays the cumulative value and this flow ends.

When determination controller 62 determines that radio field reception intensity P is higher than or equal to first threshold value a (Yes in S2), solar radiation amount obtainer 57 obtains position information from position information obtainer 53, and obtains time information indicating a current time, from timer 55 (S7). Solar radiation amount obtainer 57 obtains, from external server 13 via terminal communication unit 33 and network 11, solar radiation amount information corresponding to the obtained position information and time information (S7). The amount of solar radiation indicated by the solar radiation amount information is received-light amount q of terminal device 3.

Next, determination controller 62 determines whether or not radio field reception intensity P is lower than second threshold value b (S8).

When determination controller 62 determines that radio field reception intensity P is lower than second threshold value b (Yes in S8), received-light amount calculator 59 obtains received-light amount q of terminal device 3 from solar radiation amount obtainer 57, and calculates first corrected received-light amount obtained by correcting, using the first correction coefficient function, received-light amount q of terminal device 3 indicated by the solar radiation amount information (S9). More specifically, received-light amount calculator 59 calculates first correction coefficient k1 in accordance with radio field reception intensity P, based on the first correction coefficient function (S9). Received-light amount calculator 59 multiplies first correction coefficient k1 by received-light amount q of terminal device 3, and calculates the first corrected received-light amount. Then, received-light amount calculator 59 proceeds to steps S3 to S6, calculates a cumulative value by adding the received lighting-apparatus light amount to the first corrected received-light amount, and outputs the calculated cumulative value to determination controller 62. Determination controller 62 causes display 31 to display the cumulative value. Then, determination controller 62 returns to step S1 and carries out the same operation.

When determination controller 62 determines that radio field reception intensity P is higher than or equal to second threshold value b (No in S8), received-light amount calculator 59 calculates the second corrected received-light amount obtained by correcting, using the first correction coefficient function, received-light amount q of terminal device 3 indicated by the solar radiation amount information (S10). More specifically, received-light amount calculator 59 calculates second correction coefficient k2 in accordance with radio field reception intensity P, based on the first correction coefficient function (S10). Received-light amount calculator 59 multiplies second correction coefficient k2 by received-light amount q of terminal device 3, and calculates the second corrected received-light amount. Then, received-light amount calculator 59 proceeds to steps S3 to S6, calculates a cumulative value by adding the received lighting-apparatus light amount to the second corrected received-light amount, and outputs the calculated cumulative value to determination controller 62. Determination controller 62 causes display 31 to display the cumulative value. Then, determination controller 62 returns to step S1 and carries out the same operation.

Note that the calculation of a cumulative value performed using this flowchart may be carried out, for example, once every two days or for each predetermined time period in one day.

In this way, cumulative received-light amount estimation apparatus 5 calculates, in steps S2 to S4 of the flowchart, the received lighting-apparatus light amount which is an amount of light that is emitted by lighting apparatus 7 indoors and that the user has been able to be exposed to, when the user is indoors where the sunlight hardly comes in. Moreover, when the user is either indoors, e.g., near a window that lets the sunlight in, or outdoors, e.g., under the shade of a tree, cumulative received-light estimation apparatus 5 makes corrections using first correction coefficient k1 and calculates the first corrected received-light amount, in step S2 and steps S7 to S9 of the flowchart. Furthermore, when the user is outdoors where he/she is exposed directly to the sunlight, cumulative received-light estimation apparatus 5 makes corrections using second correction coefficient k2 and calculates the second corrected received-light amount, in steps S2, S7, S8, and S10 of the flowchart. It is thus possible to estimate a total amount of light which the user has been exposed to in one day, by adding, where necessary, the received lighting-apparatus light amount, the first corrected received-light amount, and the second corrected received-light amount, and thereby calculating a cumulative value.

Next, a method for calculating a cumulative value of the amounts of light which the user has been exposed to in one day will be described using a concrete example illustrated in FIG. 5. FIG. 5 is an explanatory diagram illustrating an example of the calculation of the cumulative value of the amounts of light which the user has been exposed to in one day.

Position information obtainer 53 generates position information indicating a living room at home where the user is present, and outputs the generated position information to solar radiation amount obtainer 57. Timer 55 generates time information indicating 06:30-07:30, and outputs the generated time information to solar radiation amount obtainer 57. Solar radiation amount obtainer 57 associates the time information indicating 06:30-07:30 to the position information indicating a living room at home. Solar radiation amount obtainer 57 obtains, from server 13, solar radiation amount information indicating 500 lx as illuminance in the case where the user is present in a living room at home from 06:30 to 07:30, and outputs the obtained solar radiation amount information to received-light amount calculator 59. Received-light amount calculator 59 calculates, for example, first correction coefficient k1 based on the radio field reception intensity of terminal device 3 obtained from reception intensity calculator 61. Received-light amount calculator 59 calculates received lighting-apparatus light amount 250 lx·h resulting from first correction coefficient k1 (k1=0.5 is assumed here)×1 h×500 lx, based on first correction coefficient k1, the time information indicating 06:30-07:30, and information indicating 500 lx as received lighting-apparatus light amount, and outputs information indicating the calculated received lighting-apparatus light amount to cumulative value calculator 63. Cumulative value calculator 63 calculates cumulative value 250 lx·h. Cumulative value calculator 63 stores this cumulative value.

Next, position information obtainer 53 generates position information indicating outdoors where the user is present, and outputs the generated position information to solar radiation amount obtainer 57. Timer 55 generates time information indicating 07:30-08:30, and outputs the generated time information to solar radiation amount obtainer 57. Solar radiation amount obtainer 57 associates the time information indicating 07:30-08:30 to the position information indicating outdoors. Solar radiation amount obtainer 57 obtains, from server 13, solar radiation amount information indicating 4,000 lx as illuminance in the case where the user is outdoors from 07:30 to 08:30, and outputs the obtained solar radiation amount information to received-light amount calculator 59. Received-light amount calculator 59 calculates, for example, second correction coefficient k2 based on the radio field reception intensity of terminal device 3 obtained from reception intensity calculator 61. Received-light amount calculator 59 calculates the second corrected received-light amount 4,000 lx·h resulting from k2 (k2=1 is assumed here)×1 h×4,000 lx, based on second correction coefficient k2, the time information indicating 0730-08:30, and the solar radiation amount information indicating 4,000 lx, and outputs information indicating the calculated second corrected received-light amount to cumulative value calculator 63. Cumulative value calculator 63 calculates cumulative value 4,250 lx·h resulting from 250 lx·h+4,000 lx·h.

Next, determination controller 62 associates light receiving period information indicating 08:30-12:00 with information indicating the brightness of light which terminal device 3 has received in an office where the brightness of light is 300 lx, and outputs the associated information to received-light amount calculator 59. Received-light amount calculator 59 calculates, for example, correction coefficient k0 based on the radio field reception intensity of terminal device 3 obtained from reception intensity calculator 61. Received-light amount calculator 59 calculates received lighting-apparatus light amount 1,050 lx·h resulting from k0×amount of solar radiation+3.5 h×300 lx, based on correction coefficient k0, the time information indicating 08:30-12:00, and the information indicating 300 lx as the brightness of the light illuminated in the office, and outputs information indicating the calculated received lighting-apparatus light amount to cumulative value calculator 63. Cumulative value calculator 63 calculates cumulative value 5,300 lx·h resulting from 4,250 lx·h+1,050 lx·h.

Next, determination controller 62 associates light receiving period information indicating 12:00-13:00 with information indicating the brightness of light which terminal device 3 has received in a restaurant where the brightness of light is 200 lx, and outputs the associated information to received-light amount calculator 59. Received-light amount calculator 59 calculates, for example, correction coefficient k0 based on the radio field reception intensity of terminal device 3 obtained from reception intensity calculator 61. Received-light amount calculator 59 calculates received lighting-apparatus light amount 200 lx·h resulting from k0 (k0=0 is assumed here)×amount of solar radiation+1 h×200 lx, based on correction coefficient k0, the time information indicating 12:00-13:00, and the information indicating 200 lx as the brightness of the light illuminated in the restaurant, and outputs information indicating the calculated received lighting-apparatus light amount to cumulative value calculator 63. Cumulative value calculator 63 calculates cumulative value 5,500 lx·h resulting from 5,300 lx·h+200 lx·h.

Next, determination controller 62 associates light receiving period information indicating 13:00-18:00 with information indicating the brightness of light which terminal device 3 has received in the office where the brightness of light is 300 lx, and outputs the associated information to received-light amount calculator 59. Received-light amount calculator 59 calculates, for example, correction coefficient k0 based on the radio field reception intensity of terminal device 3 obtained from reception intensity calculator 61. Received-light amount calculator 59 calculates received lighting-apparatus light amount 1500 lx·h resulting from k0 (k0=0 is assumed here)×amount of solar radiation+5 h×300 lx, based on correction coefficient k0, the time information indicating 13:00-18:00, and the information indicating 300 lx as the brightness of the light illuminated in the office, and outputs information indicating the calculated received lighting-apparatus light amount to cumulative value calculator 63. Cumulative value calculator 63 calculates cumulative value 7,000 lx·h resulting from 5,500 lx·h+1,500 lx·h.

Next, position information obtainer 53 generates position information indicating outdoors where the user is present, and outputs the generated position information to solar radiation amount obtainer 57. Timer 55 generates time information indicating 18:00-19:00, and outputs the generated time information to solar radiation amount obtainer 57. Solar radiation amount obtainer 57 associates the position information indicating outdoors with the time information indicating 18:00-19:00. Solar radiation amount obtainer 57 obtains, from server 13, solar radiation amount information indicating 100 lx as illuminance in the case where the user is outdoors from 18:00 to 19:00, and outputs the obtained solar radiation amount information to received-light amount calculator 59. Received-light amount calculator 59 calculates, for example, first correction coefficient k1 based on the radio field reception intensity of terminal device 3 obtained from reception intensity calculator 61. Received-light amount calculator 59 calculates the first corrected received-light amount 10 lx·h resulting from k1 (k1=0.1 is assumed here)×1 h×100 lx, based on first correction coefficient k1, the time information indicating 18:00-19:00, and the solar radiation amount information indicating 100 lx, and outputs information indicating the calculated first corrected received-light amount to cumulative value calculator 63. Cumulative value calculator 63 calculates cumulative value 7,010 lx·h resulting from 7,000 lx·h+10 lx·h.

Next, determination controller 62 associates light receiving period information indicating 19:00-23:00 with information indicating the brightness of light which terminal device 3 has received in the living room at home where the brightness of light is 200 lx, and outputs the associated information to received-light amount calculator 59. Received-light amount calculator 59 calculates, for example, correction coefficient k0 based on the radio field reception intensity of terminal device 3 obtained from reception intensity calculator 61. Received-light amount calculator 59 calculates received lighting-apparatus light amount 800 lx·h resulting from k0 (k0=0 is assumed here)× amount of solar radiation+4 h×200 lx, based on correction coefficient k0, the time information indicating 19:00-23:00, and the information indicating 200 lx as the brightness of the light illuminated in the living room at home, and outputs information indicating the calculated received lighting-apparatus light amount to cumulative value calculator 63. Cumulative value calculator 63 calculates cumulative value 7,810 lx·h resulting from 7,010 lx·h+800 lx·h.

After that, the user is asleep until 06:30 the next day, therefore, cumulative value calculator 63 calculates a cumulative value 7,810 lx·h resulting from 7,010 lx·h+800 lx·h. Then, cumulative value calculator 63 outputs information indicating the cumulative value 7810 lx·h to determination controller 62, and causes display 31 to display the cumulative value 7810 lx·h. This enables the user to know the cumulative value of the amounts of light he/she has been exposed to in one day. Note that, in the description of FIG. 5, determination controller 62 calculates a cumulative value for each predetermined time period but determination controller 62 may cause display 31 to display a cumulative value each time a cumulative value is calculated, or may calculate a cumulative value every second, every minute, etc, and cause display 31 to display the calculated cumulative value in the same manner. Accordingly, a timing to calculate a cumulative value and a timing to cause display 31 to display a cumulative value are not limited to the timings described in this embodiment.

Solar radiation amount obtainer 57 of cumulative received-light amount estimation apparatus 5 thus obtains solar radiation amount information based on time information and position information. Through the determination made by determination controller 62 based on the radio field reception intensity calculated by reception intensity calculator 61, received-light amount calculator 59 calculates a corrected received-light amount by correcting an amount of solar radiation indicated by the solar radiation amount information It is therefore possible to precisely calculate, without a sensor or the like worn on the user's body, a cumulative value of the amounts of light which terminal device 3 has received.

Advantageous Effects

The following describes the advantageous effects of a cumulative received-light amount estimation method, a program, cumulative received-light amount estimation apparatus 5, and health care system 1 according to the present embodiment.

As has been described above, the cumulative received-light amount estimation method according to the present embodiment includes: receiving, by terminal device 3, position information of terminal device 3 via a wireless signal, and time information; obtaining solar radiation amount information corresponding to the position information of a device and the time information, the solar radiation amount information indicating an amount of solar radiation corresponding to the position information of terminal device 3 and the time information; calculating a corrected received-light amount by correcting the amount of solar radiation, based on a radio field reception intensity of the wireless signal that includes the position information, the amount of solar radiation being indicated by the solar radiation amount information; and obtaining, by terminal device 3, a cumulative value of amounts of light which a user of the device has been exposed to, using the corrected received-light amount.

According to this method, a corrected received-light amount is calculated by correcting an amount of solar radiation indicated by the solar radiation amount information, based on a radio field reception intensity, and a cumulative value of the amounts of light which the user of terminal device 3 has been exposed to is obtained by terminal device 3 using the corrected received-light amount. It is therefore possible to precisely estimate the amount of light which the user has been exposed to, based on position information and time information, without causing the user to wear a detecting device such as a sensor.

Accordingly, with such a cumulative received-light amount estimation method, it is possible, without the use of a sensor, to precisely estimate a cumulative value of the amounts of light which the user has been exposed to.

Particularly because it is possible to precisely estimate a cumulative value of the amounts of light which the user has been exposed to, without a detecting device mounted on cumulative received-light amount estimation apparatus 5, rise in the manufacturing cost of cumulative received-light amount estimation apparatus 5 can be restrained.

Moreover, a non-transitory computer readable medium storing a program, according to the present embodiment, causes a computer to execute the aforementioned cumulative received-light amount estimation method.

Further, cumulative received-light amount estimation apparatus 5 according to the present embodiment includes: solar radiation amount obtainer 57 that obtains solar radiation amount information corresponding to position information of terminal device 3 and time information; received-light amount calculator 59 that calculates a corrected received-light amount obtained by correcting an amount of light received by terminal device 3, based on a radio field reception intensity of a wireless signal that includes the position information, the amount of light received being indicated by the solar radiation amount information; and cumulative value calculator 63 that calculates a cumulative value that includes the corrected received-light amount.

Furthermore, cumulative received-light amount estimation apparatus 5 according to the present embodiment further includes display 31 that displays the cumulative value calculated by cumulative value calculator 63.

With such program and cumulative received-light amount estimation apparatus 5, the same advantageous effects as can be gained using the cumulative received-light amount estimation method according to the present embodiment.

Moreover, in the cumulative received-light amount estimation method according to the present embodiment further includes: determining whether or not the radio field reception intensity is higher than or equal to a first threshold value and is lower than a second threshold value; calculating, as the corrected received-light amount, the first corrected received-light amount obtained by correcting the amount of solar radiation, using a first correction coefficient, the first correction coefficient being obtained by using a first correction coefficient function of the radio field reception intensity, the first correction coefficient being defined when the radio field reception intensity is higher than or equal to the first threshold value and is lower than the second threshold value; and calculating, as the corrected received-light amount, the second corrected received-light amount obtained by correcting the amount of solar radiation, using a second correction coefficient, when the radio field reception intensity is higher than or equal to the second threshold value, the second correction coefficient being greater than the first correction coefficient and being obtained by using the first correction coefficient function.

According to this method, the first corrected received-light amount or the second corrected received-light amount is calculated depending on whether or not the radio field reception intensity is higher than or equal to the first threshold value and is lower than the second threshold value. Accordingly, when the user is either indoors, e.g., near a window that lets the sunlight in, or outdoors, e.g., under the shade of a tree, the first corrected received-light amount is calculated, and when the user is outdoors where he/she is directly exposed to the sunlight, the second corrected received-light amount is calculated. Since a cumulative value can be calculated according to a place where the user is present, it is possible to precisely estimate a cumulative value of the amounts of light which the user has been exposed to.

Moreover, in the cumulative received-light amount estimation method according to the present embodiment, the first correction coefficient function is a non-decreasing function.

According to this method, it is possible to calculate each correction coefficient according to radio field reception intensity. It is therefore possible to precisely estimate a cumulative value of the amounts of light which the user has been exposed to.

Moreover, the cumulative received-light amount estimation method according to the present embodiment further includes: determining whether or not information indicating a received lighting-apparatus light amount is obtainable by terminal device 3, the received lighting-apparatus light amount being an amount of light which is emitted by lighting apparatus 7 and which the user of terminal device 3 has been exposed to. In the calculating of the cumulative value, when the information indicating the received lighting-apparatus light amount is obtainable, the received lighting-apparatus light amount is added to the corrected received-light amount.

According to this method, in the calculating of the cumulative value, when the information indicating the received lighting-apparatus light amount is obtainable, the received lighting-apparatus light amount is added to the corrected received-light amount. It is therefore possible to precisely estimate a cumulative value of the amounts of light which the user has been exposed to.

The cumulative received-light amount estimation method according to the present embodiment further includes: determining whether or not brightness of light emitted by the lighting apparatus is higher than or equal to a predetermined value. In the calculating of the cumulative value, when the received lighting-apparatus light amount is smaller than a predetermined value, the received lighting-apparatus light amount is not added to the corrected received-light amount, and when the received-lighting-apparatus light amount is greater than or equal to the predetermined value, the received lighting-apparatus light amount is added to the corrected received-light amount.

According to this method, in the calculating of the cumulative value, when the received lighting-apparatus light amount is smaller than a predetermined value, the received lighting-apparatus light amount is not added to the corrected received-light amount, and when the received-lighting-apparatus light amount is greater than or equal to the predetermined value, the received lighting-apparatus light amount is added to the corrected received-light amount. Since a cumulative value does not include a received-light amount from which the effect of correcting a biological rhythm cannot be expected, the user can correctly know an amount of received-light effective for correcting a biological rhythm.

The cumulative received-light amount estimation method according to the present embodiment further includes: storing schedule information of a user including scheduled position information and scheduled time information; and calculating solar radiation amount information corresponding to the scheduled position information and the scheduled time information.

According to this method, by previously storing, for example, schedule information of one day, solar radiation amount information corresponding to scheduled position information and scheduled time information are obtained based on position information and time information that are associated with the schedule information. With the schedule information, it is therefore possible to omit a process of calculating a corrected received-light amount obtained by correcting an amount of light that is received by terminal device 3 and is indicated by the solar radiation amount information. Therefore, in the case of applying the cumulative received-light amount estimation method to terminal device 3, for example, it is possible to simplify the processing of terminal device 3.

In addition, in the cumulative received-light amount estimation method according to the present embodiment, the corrected received-light amount is calculated by using a function of the radio field reception intensity.

Moreover, in the cumulative received-light amount estimation method according to the present embodiment, the function is a non-decreasing function.

Furthermore, in the cumulative received-light amount estimation method according to the present embodiment, the first correction coefficient function becomes constant at or over the second threshold value.

Still further, in the cumulative received-light amount estimation method according to the present embodiment, the second corrected received-light amount is calculated using a third correction coefficient, when the radio field reception intensity is lower than the first threshold value, the third correction coefficient being obtained by using the first correction coefficient function.

What is more, in the cumulative received-light amount estimation method according to the present embodiment, the first correction coefficient function becomes zero at or below the first threshold value.

Furthermore, the cumulative received-light amount estimation method according to the present embodiment further includes: obtaining water vapor information which indicates an amount of water vapor in air and corresponds to position information and time information; and correcting the radio field reception intensity by using the water vapor information.

Moreover, health care system 1 according to the present embodiment includes: cumulative received-light amount estimation apparatus 5; managing computer 67 that manages an amount of light which a user is exposed to, a health condition of the user, and a sleeping condition of the user, based on the cumulative value obtained from the cumulative received-light amount estimation apparatus; and lighting apparatus 7.

According to this, managing computer 67 manages an amount of light which the user is exposed to, according to a cumulative value. It is therefore possible to manage the health condition and sleeping condition of the user. It is therefore possible to appropriately regulate the biological rhythm of the user.

In health care system 1 according to the present embodiment, managing computer 67 controls at least one of brightness of light emitted by lighting device 7 and a light emitting period of lighting device 7, based on an amount of light the user is exposed to, information indicating the health condition of the user, and information indicating the sleeping condition of the user.

According to this, managing computer 67 controls at least one of the brightness of light emitted by lighting apparatus 7 and the light emitting period of lighting apparatus 7, based on an amount of light which the user is exposed to, on information indicating the health condition of the user, and on information indicating the sleeping condition of the user. It is therefore possible to appropriately regulate the biological rhythm of the user.

Furthermore, in health care system 1 according to the present embodiment, when an amount of light which the user has been exposed to in one day is less than a value that is previously set, managing computer 67 performs, for the following day, at least one of increasing the brightness of light emitted by lighting apparatus 7 and extending the light emitting period of lighting apparatus 7.

Embodiment 2

Figure 6:
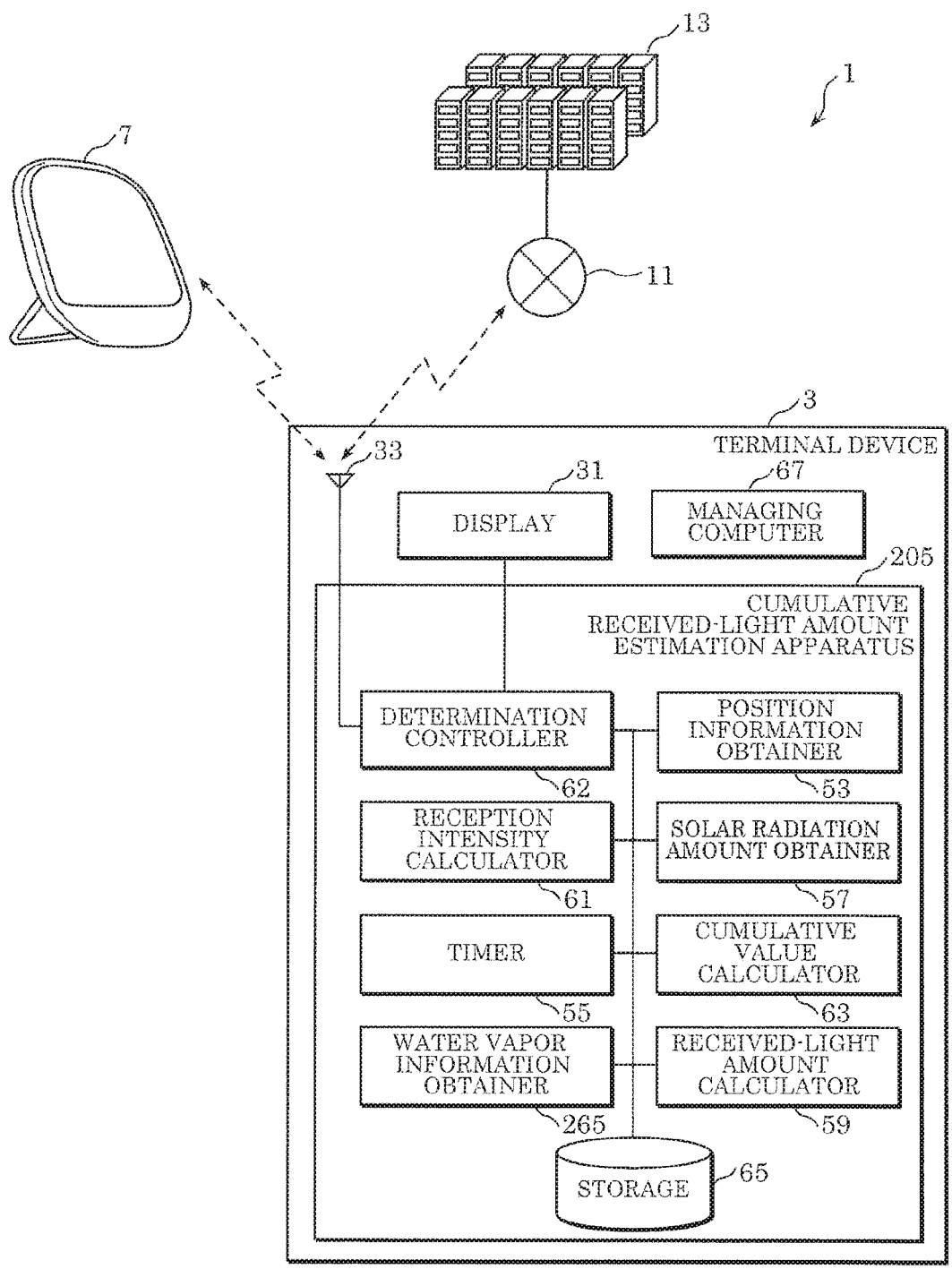
FIG. 6 is a block diagram illustrating a health care system according to Embodiment 2.

The following describes, with reference to FIG. 6, the configuration of health care system 1 according to the present embodiment.

FIG. 6 is a block diagram illustrating health care system 1 according to Embodiment 2.

The present embodiment differs from Embodiment 1 in that cumulative received-light amount estimation apparatus 205 includes water vapor information obtainer 265 and also in that reception intensity calculator 61 corrects a radio field reception intensity based on water vapor information. Moreover, particularly where it is not explicitly stated, cumulative received-light amount estimation apparatus 205 has the same configuration as cumulative received-light amount estimation apparatus 5 described in Embodiment 1, the identical components are assigned the same reference signs, and the detailed description of the components is omitted.

As illustrated in FIG. 6, position information obtainer 53 outputs the obtained position information to solar radiation amount obtainer 57, water vapor information obtainer 265, etc. Moreover, timer 55 measures a current time and outputs the measured current time to determination controller 62, solar radiation amount obtainer 57, water vapor information obtainer 265, etc.

Water vapor information obtainer 265 obtains the position information of terminal device 3 from position information obtainer 53, and time information corresponding to the obtained position information, from timer 55. Water vapor information obtainer 265 associates the obtained position information of terminal device 3 with the obtained time information. Note that when position information has already been associated with time information, that is, when position information obtainer 53 obtains information in which position information and time information are associated with each other, water vapor information obtainer 265 need not associate position information with time information. Water vapor information obtainer 265 obtains, from server 13 via terminal communication unit 33 and network 11, water vapor information which indicates an amount of water vapor in the air and corresponds to position information and time information. Water vapor information obtainer 265 outputs the obtained water vapor information to reception intensity calculator 61. The water vapor information indicates an amount of water vapor in the vicinity of terminal device 3. Server 13 described in this embodiment includes not only a meteorological institute but also a national astronomical observatory or the like, and water vapor information obtainer 265 obtains water vapor information from information officially announced by a national astronomical observatory or the like.

Reception intensity calculator 61 detects a current radio field reception intensity of terminal communication unit 33. Reception intensity calculator 61 calculates the first corrected reception intensity, the second corrected reception intensity, or the third corrected reception intensity which is obtained by correcting a radio field reception intensity using the second correction coefficient function.

Figure 7:
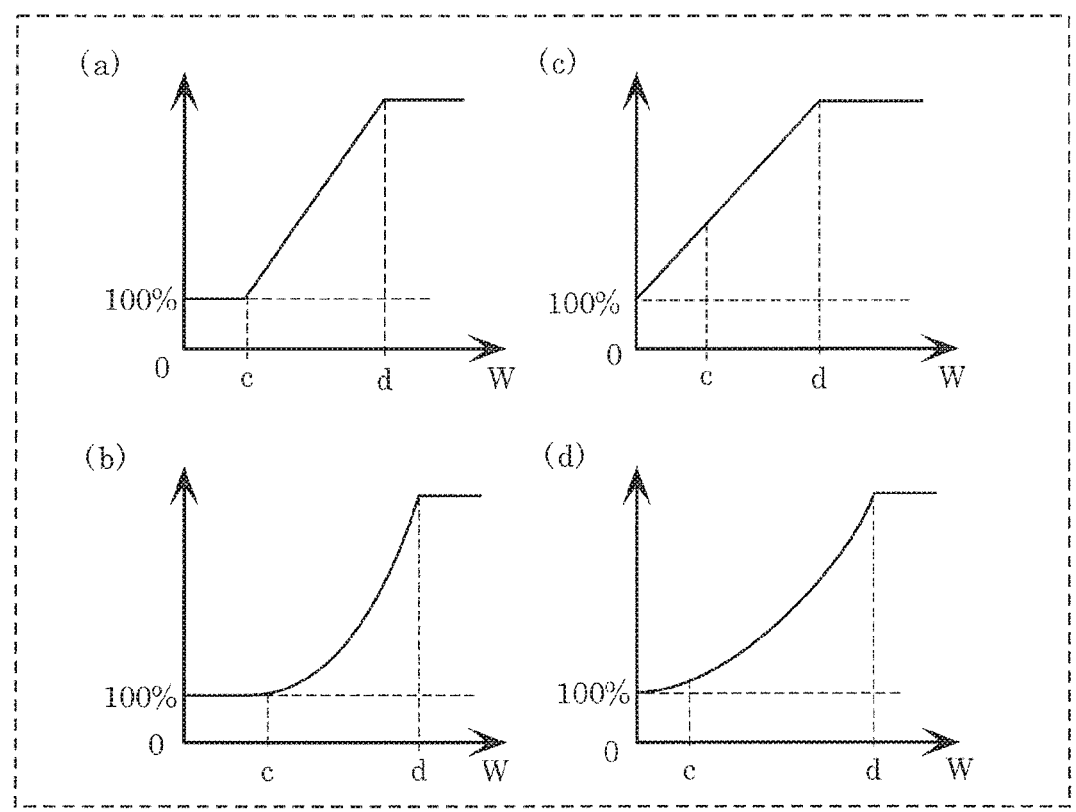
FIG. 7 is a diagram illustrating examples of the second correction coefficient function to be used by a cumulative received-light amount estimation apparatus according to Embodiment 2.

The second correction coefficient function is a non-decreasing function and is illustrated, for example, in FIG. 7. FIG. 7 is a diagram illustrating examples of the second correction coefficient function to be used by cumulative received-light amount estimation apparatus 205 according to Embodiment 2. A line represented m the second correction coefficient function may be curved, straight, or stepwise, or may be an arbitrary combination of these. In FIG. 7, a vertical axis represents a correction coefficient while a horizontal line represents an amount of water vapor. Third correction coefficient k3, fourth correction coefficient k4, and fifth correction coefficient k5 are each calculated based on this second correction coefficient function.

Referring to (a) in FIG. 7 as an example, third correction coefficient k3 of the amount of water vapor, which is defined when an amount of water vapor is lower than third threshold value c, becomes 100%. That is to say, k3=1. Moreover, when an amount of water vapor is higher than or equal to third threshold value c and is lower than fourth threshold value d, fourth correction coefficient k4 is derived based on a range of from third threshold value c to fourth threshold value d, and fourth correction coefficient k4 indicates a value greater than or equal to 1. Furthermore, when an amount of water vapor is higher than or equal to the fifth threshold value, fifth correction coefficient k5 indicates a value higher than 100%. In other words, fifth correction coefficient k5 indicates a value greater than fourth correction coefficient k4.

When the amount of water vapor is lower than third threshold value c, the weather is estimated to be fine, the amount of water vapor in the air is small, and terminal device 3 is placed in an environment where the radio field intensity of terminal device 3 hardly decreases. In this case, since the water vapor hardly gives influence to radio field environment, third correction coefficient k3 derived using the second correction coefficient function indicates a value that is greater than or equal to 1 and is approximated to 1.

When the amount of water vapor is higher than or equal to third threshold value c and is lower than fourth threshold value d, the weather is estimated to be slightly cloudy, the amount of water vapor in the air is about mediate, and terminal device 3 is placed in an environment where the radio field intensity of terminal device 3 easily and slightly decreases compared to the case where the weather is fine. In this case, since the water vapor gives influence to radio field environment, fourth correction coefficient k4 derived using the second correction coefficient function indicates a value that is greater than third correction coefficient k3.

When the amount of water vapor is higher than or equal to fourth threshold value d, the weather is estimated to be cloudy or rainy, the amount of water vapor m the air is large, and terminal device 3 is placed in an environment where the radio field intensity of terminal device 3 easily decreases. In this case, since the water vapor gives influence to radio field environment, fifth correction coefficient k5 derived using the second correction coefficient function indicates a value that is greater than fourth correction coefficient k4.

As illustrated in FIG. 6, reception intensity calculator 61 calculates the first corrected reception intensity by multiplying a radio field reception intensity by third correction coefficient k3, calculates the second corrected reception intensity by multiplying a radio field reception intensity by fourth correction coefficient k4, and calculates the third corrected reception intensity by multiplying a radio field reception intensity by fifth correction coefficient k5. Reception intensity calculator 61 outputs, to cumulative value calculator 63, respective information regarding the first corrected reception intensity, the second corrected reception intensity, and the third corrected reception intensity that have been calculated. The radio field reception intensity includes the first corrected reception intensity, the second corrected reception intensity, and the third corrected reception intensity.

Determination controller 62 determines whether or not the amount of water vapor is higher than or equal to the third threshold value and is lower than the fourth threshold value. In the case of determining that the amount of water vapor is lower than the third threshold value, reception intensity calculator 61 calculates the first corrected reception intensity by correcting a radio field reception intensity using the third correction coefficient derived with use of the second correction coefficient function.

In the case of determining that the amount of water vapor is higher than or equal to the third threshold value and is lower than the fourth threshold value, reception intensity calculator 61 calculates the second corrected reception intensity by correcting a radio field reception intensity using the fourth correction coefficient which is greater than the third correction coefficient derived with use of the second correction coefficient function.

In the case of determining that the amount of water vapor is higher than or equal to the fourth threshold value, reception intensity calculator 61 calculates the third corrected reception intensity by correcting a radio field reception intensity using the fifth correction coefficient which is greater than the fourth correction coefficient derived with use of the second correction coefficient function.

[Operation]

The following describes the operation of cumulative received-light amount estimation apparatus 205.

Figure 8:
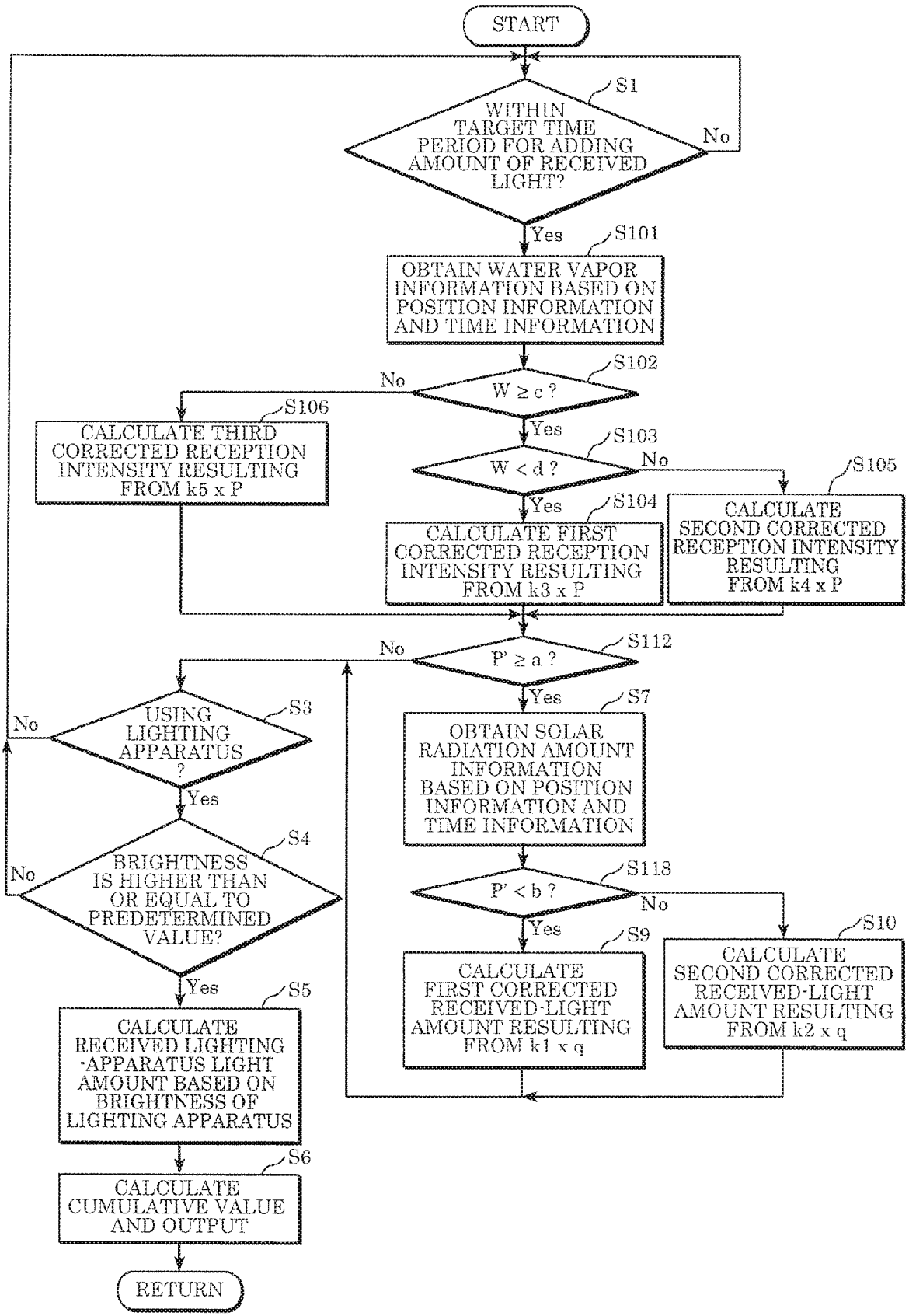
FIG. 8 is a flowchart illustrating an operation performed by the cumulative received-light amount estimation apparatus according to Embodiment 2.

FIG. 8 is a flowchart illustrating the operation of cumulative received-light amount estimation apparatus 205 according to Embodiment 2.

As illustrated in FIG. 8, determination controller 62 firstly determines whether or not a current time is within a target time period for adding an amount of received light (S1). In the case of determining that the current time is not within the target time period (No in S1), determination controller 62 returns to step S1 and carries out the same process for determination.

On the contrary, when determination controller 62 determines that the current time is within the target time period (Yes in S1), reception intensity calculator 61 obtains position information from position information obtainer 53 and time information from timer 55 (S101). Reception intensity calculator 61 obtains, from server 13 via terminal communication unit 33 and network 11, water vapor amount W indicated by water vapor information corresponding to the obtained position information and time information (S101).

Determination controller 62 subsequently determines whether or not water vapor amount W obtained in step S101 is higher than or equal to third threshold value c (S102).

In the case of determining that water vapor amount W obtained in step S101 is higher than or equal to third threshold value c (Yes in S102), determination controller 62 determines whether or not water vapor amount W obtained in step S101 is lower than fourth threshold value d (S103).

When determination controller 62 determines that water vapor amount W obtained in step S101 is lower than fourth threshold value d (Yes in S103), reception intensity calculator 61 calculates the first corrected reception intensity obtained by correcting radio field reception intensity P, using the second correction coefficient function (S104). More specifically, reception intensity calculator 61 calculates third correction coefficient k3 in accordance with water vapor amount W, based on the second correction coefficient function. Reception intensity calculator 61 multiplies third correction coefficient k3 by radio field reception intensity P, and thereby calculates the first corrected reception intensity.

On the contrary, when determination controller 62 determines that water vapor amount W obtained in step S101 is higher than or equal to fourth threshold value d (No in S103), reception intensity calculator 61 calculates the second corrected reception intensity obtained by correcting radio field reception intensity P, using the second correction coefficient function (S105). More specifically, reception intensity calculator 61 calculates fourth correction coefficient k4 in accordance with water vapor amount W, based on the second correction coefficient function. Reception intensity calculator 61 multiplies fourth correction coefficient k4 by radio field reception intensity P, and thereby calculates the second corrected reception intensity.

When determination controller 62 determines that water vapor amount W obtained in step S101 is lower than third threshold value c (No in S102), reception intensity calculator 61 calculates the third corrected reception intensity obtained by correcting radio field reception intensity P, using the second correction coefficient function (S106). More specifically, reception intensity calculator 61 calculates fifth correction coefficient k5 in accordance with water vapor amount W, based on the second correction coefficient function. Reception intensity calculator 61 multiplies fifth correction coefficient k5 by radio field reception intensity P, and thereby calculates the third corrected reception intensity.

Next, determination controller 62 determines whether or not radio field reception intensity P is higher than or equal to first threshold value a (S112). Radio field reception intensity P is first corrected reception intensity P2, the second corrected reception intensity or the third corrected reception intensity obtained in the correction in step S104, S105, or S106 after the determination in step S103. Therefore, in the case of having passed through step S104, determination controller 62 determines whether or not the first corrected reception intensity is higher than or equal to first threshold value a in step S112 (S112). Moreover, in the case of having passed through step S105, determination controller 62 determines whether or not the second corrected reception intensity is higher than or equal to first threshold value a in step S112 (S112). Further, in the case of having passed through step S106, determination controller 62 determines whether or not the third corrected reception intensity is higher than or equal to first threshold value a in step S112 (S112). In FIG. 8, first corrected reception intensity P2, the second corrected reception intensity, and the third corrected reception intensity are collectively called radio field reception intensity P'.

In the case of determining that radio field reception intensity P' is lower than first threshold value a (No in S112), determination controller 62 carries out steps S3 to S6 of the flowchart in FIG. 4, and in step S6, cumulative value calculator 63 adds received lighting-apparatus light amount to the first corrected received-light amount, and thereby calculates a cumulative value. Then, determination controller 62 outputs the calculated cumulative value to display 31. With this, display 31 displays the cumulative value, and the flow ends.

In the case of determining that radio field reception intensity P' is higher than or equal to first threshold value a (Yes in S112), determination controller 62 obtains position information from position information obtainer 53, and time information indicating a current time, from timer 55 (S7). Solar radiation amount obtainer 57 obtains, from external server 13 via terminal communication unit 33 and network 11, received-light amount q of terminal device 3 indicated by solar radiation amount information corresponding to the obtained position information and time information (S7). Solar radiation amount obtainer 57 outputs the obtained solar radiation amount information to received-light amount calculator 59.

Next, determination controller 62 determines whether or not radio field reception intensity P' is lower than second threshold value b (S118).

When determination controller 62 determines that radio field reception intensity P' is lower than second threshold value b (Yes in S118), received-light amount calculator 59 obtains received-light amount q of terminal device 3 from solar radiation amount obtainer 57, and calculates first corrected received-light amount obtained by correcting received-light amount q of terminal device 3, which is indicated by the solar radiation amount information, using the first correction coefficient function (S9). More specifically, received-light amount calculator 59 calculates first correction coefficient k1 in accordance with radio field reception intensity P based on the first correction coefficient function. Received-light amount calculator 59 multiplies first correction coefficient k1 by received-light amount q of terminal device 3, and thereby calculates the first corrected received-light amount. Determination controller 62 then proceeds to step S3 and carries out the same operation.

When determination controller 62 determines that radio field reception intensity P' is higher than or equal to second threshold value b (No in S8), received-light amount calculator 59 calculates the second corrected received-light amount obtained by correcting received-light amount q of terminal device 3, which is indicated by the solar radiation amount information, using the first correction coefficient function. More specifically, received-light amount calculator 59 calculates second correction coefficient k2 in accordance with radio field reception intensity P' based on the first correction coefficient function. Received-light amount calculator 59 multiplies second correction coefficient k2 by received-light amount q of terminal device 3, and thereby calculates the second corrected received-light amount. Determination controller 62 returns to step S1 after going through steps S3 to S6, and carries out the same process for determination.

Advantageous Effects

The following describes the advantageous effects of the cumulative received-light amount estimation method, the program, cumulative received-light amount estimation apparatus 205, and health care system 1 according to the present embodiment.

As has been described above, in the cumulative received-light amount estimation method according to the present embodiment, the radio field reception intensity includes the first corrected reception intensity, the second corrected reception intensity, and the third corrected reception intensity. The cumulative received-light estimation method further includes: determining whether or not the amount of water vapor is higher than or equal to a third threshold value and is lower than a fourth threshold value; calculating the first corrected reception intensity obtained by correcting the radio field reception intensity, using a third correction coefficient obtained by using a second correction coefficient function of the amount of water vapor, the second correction coefficient function being defined when the amount of water vapor is lower than the third threshold value; calculating the second corrected reception intensity obtained by correcting the radio field reception intensity, using a fourth correction coefficient that is greater than the third correction coefficient, when the amount of water vapor is higher than or equal to the third threshold value and is lower than the fourth threshold value, the third correction coefficient being derived with use of the second correction coefficient function; and calculating the third corrected reception intensity obtained by correcting the radio field reception intensity using a fifth correction coefficient that is greater than the fourth correction coefficient, when the amount of water vapor is higher than or equal to the fourth threshold value, the fourth correction coefficient being derived with use of the second correction coefficient function.

According to this method, it is possible to derive the third correction coefficient, the fourth correction coefficient, and the fifth correction coefficient according to the amount of water vapor, using the second correction coefficient function. With this method, it is possible to correct a radio field reception intensity using the third correction coefficient, the fourth correction coefficient, or the fifth correction coefficient, and to calculate the first corrected reception intensity, the second corrected reception intensity, or the third corrected reception intensity. With this method, it is also possible, based on the first corrected reception intensity, the second corrected reception intensity, or the third corrected reception intensity, to calculate a corrected received-light amount obtained by correcting an amount of light received by terminal device 3, which is indicated by the solar radiation amount information. Therefore, with this method, it is possible to more precisely estimate a cumulative value of the amounts of light which the user has been exposed to.

Moreover, in the cumulative received-light amount estimation method according to the present embodiment, the second correction coefficient function is a non-decreasing function.

According to this method, it is possible to calculate each correction coefficient according to radio field reception intensity. It is therefore possible to precisely estimate a cumulative value of the amounts of light which the user has been exposed to.

As for other advantageous effects gained according to the present embodiment, the same effects as those described in Embodiment 1 can be gained.

Variations and Others

While the present disclosure has been described based on Embodiment 1 and Embodiment 2, the present disclosure shall not be limited to aforementioned Embodiments 1 and 2.

For example, in the cumulative received-light amount estimation method, program, cumulative received-light amount estimation apparatus, and health care system according to aforementioned Embodiments 1 and 2, (b), (c), and (d) in FIG. 2 are other examples of (a) in FIG. 2 indicating the first correction coefficient function. Moreover, (b), (c), and (d) in FIG. 7 are other examples of (a) in FIG. 7 indicating the second correction coefficient function. Note that (b), (c), and (d) in FIG. 2 illustrating the examples of the first correction coefficient function and (b), (c), and (d) in FIG. 7 illustrating the examples of the second correction coefficient function are mere examples, and the first and second correction coefficient functions are not limited to such.

Further, in the cumulative received-light amount estimation method, program, cumulative received-light amount estimation apparatus and health care system according to aforementioned Embodiments 1 and 2, even with the use of a lighting apparatus, information indicating the brightness of the lighting apparatus cannot be obtained from the lighting apparatus, in some cases. In this case, a determination controller causes a display to display a form for user's subjective assessment and causes the user to input his/her subjective assessment via an input unit included in a terminal device. Thus, an amount of light which the user has been exposed to may be estimated.

Furthermore, in the cumulative received-light amount estimation method, program, cumulative received-light amount estimation apparatus, and health care system according to aforementioned Embodiments 1 and 2, with the cumulative received-light amount estimation apparatus, the calculation of a cumulative value is not restricted to one day, and it is possible to calculate a cumulative value of the amounts of light received over a specific time period.

Each of the cumulative received-light amount estimation method, program, cumulative received-light amount estimation apparatus, and health care system according to aforementioned Embodiments 1, and 2 is typically realized as an LSI which is an integrated circuit. These circuits may be individually realized as one chip or may be realized as one chip including part or all of the circuits.

Further, each of the cumulative received-light amount estimation method, program, cumulative received-light amount estimation apparatus, and health care system according to aforementioned Embodiments 1 and 2 to be realized as an integrated circuit is not limited to LSI, and each of them may be realized as a dedicated circuit or a general-purpose processor. An FPGA (Field Programmable Gate Array) which can be programmed after an LSI is manufactured or a reconfigurable processor which can reconfigure connection or setting of circuit cells inside an LSI may be used.

Note that in each of the aforementioned Embodiments 1 and 2, each component may be configured by dedicated hardware or may be realized by executing a software program suitable for each component. Each component may be realized by causing a program executing unit such as a CPU or a processor to read a software program recorded on a recording medium such as a hard disk or a semiconductor memory and execute the software program.

Moreover, all the numbers used above are exemplary numbers to specifically describe the present disclosure, and the present disclosure is not limited to the illustrated numbers.

Further, division of a functional block in each block diagram is an example, and plural functional blocks may be realized as one functional block, one functional block may be divided into plural functional blocks, or part of functions may be transferred to another functional block. Besides, single hardware or software may process, in parallel or by way of time division, functions of plural functional blocks having similar functions.

Furthermore, an order to execute each step in the flowchart is an exemplary order for specifically describing the present disclosure, and may be other than the above-described order. Furthermore, part of the above-described steps may be executed at the same time as (in parallel to) the execution of other steps.

Thus, the cumulative received-light amount estimation method, program, cumulative received-light amount estimation apparatus, and health care system according to one or more aspects have been described based on Embodiments 1 and 2. However, the present disclosure is not limited to Embodiments 1 and 2 of the present disclosure. Forms obtained by various modifications to the foregoing embodiment that can be conceived by a person skilled in the art as well as forms realized by arbitrarily combining components and functions in the embodiment within the scope of the essence of the present disclosure are included in the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A method comprising:
receiving, by a device, position information of the device via a wireless signal, and time information;
obtaining solar radiation amount information corresponding to the position information and the time information, the solar radiation amount information indicating an amount of solar radiation corresponding to the position information of the device and the time information;
obtaining a corrected received-light amount by correcting the amount of solar radiation, based on a radio field reception intensity of the wireless signal that includes the position information, the amount of solar radiation being indicated by the solar radiation amount information; and obtaining, by the device, a cumulative value of amounts of light which a user of the device has been exposed to, using the corrected received-light amount.

2. The method according to claim 1, wherein
the corrected received-light amount is calculated by using a function of the radio field reception intensity.

3. The method according to claim 2, wherein
the function is a non-decreasing function.

4. The method according to claim 2 further comprising:
determining whether or not the radio field reception intensity is higher than or equal to a first threshold value and is lower than a second threshold value;
calculating, as the corrected received-light amount, a first corrected received-light amount obtained by correcting the amount of solar radiation, using a first correction coefficient obtained by using a first correction coefficient function of the radio field reception intensity, the first correction coefficient function being defined when the radio field reception intensity is higher than or equal to the first threshold value and is lower than the second threshold value; and
calculating, as the corrected received-light amount, a second corrected received-light amount obtained by correcting the amount of solar radiation, using a second correction coefficient, when the radio field reception intensity is higher than or equal to the second threshold value, the second correction coefficient being greater than the first correction coefficient and being obtained by using the first correction coefficient function.

5. The method according to claim 4, wherein
the first correction coefficient function is a non-decreasing function.

6. The method according to claim 4,
wherein the first correction coefficient function becomes constant at or over the second threshold value.

7. The method according to claim 4, wherein
the second corrected received-light amount is calculated using a third correction coefficient, when the radio field reception intensity is lower than the first threshold value, the third correction coefficient being obtained by using the first correction coefficient function.

8. The method according to claim 7, wherein
the first correction coefficient function becomes zero at or below the first threshold value.

9. The method according to claim 1, further comprising:
obtaining water vapor information which indicates an amount of water vapor in air and corresponds to the position information and the time information; and
correcting the radio field reception intensity by using the water vapor information.

10. The method according to claim 9, wherein
the radio field reception intensity includes a first corrected reception intensity, a second corrected reception intensity, and a third corrected reception intensity, and
the method further comprising:
determining whether or not the amount of water vapor is higher than or equal to a third threshold value and is lower than a fourth threshold value;
calculating the first corrected reception intensity obtained by correcting the radio field reception intensity, using a third correction coefficient obtained by using a second correction coefficient function of the amount of water vapor, the second correction coefficient function being defined when the amount of water vapor is lower than the third threshold value;
calculating the second corrected reception intensity obtained by correcting the radio field reception intensity, using a fourth correction coefficient that is greater than the third correction coefficient, when the amount of water vapor is higher than or equal to the third threshold value and is lower than the fourth threshold value, the third correction coefficient being obtained by using the second correction coefficient function; and
calculating the third corrected reception intensity obtained by correcting the radio field reception intensity using a fifth correction coefficient that is greater than the fourth correction coefficient, when the amount of water vapor is higher than or equal to the fourth threshold value, the fourth correction coefficient being obtained by using the second correction coefficient function.

11. The method according to claim 10, wherein
the second correction coefficient function is a non-decreasing function.

12. The method according to claim 1, further comprising:
determining whether or not information indicating a received lighting-apparatus light amount is obtainable by the device, the received lighting-apparatus light amount being an amount of light which is emitted by a lighting apparatus and which the user of the device has been exposed to,
wherein in the obtaining of the cumulative value, when the information indicating the received lighting-apparatus light amount is obtainable, the received lighting-apparatus light amount is added to the corrected received-light amount.

13. The method according to claim 12, further comprising:
determining whether or not brightness of light emitted by the lighting apparatus is higher than or equal to a predetermined value, wherein
in the obtaining of the cumulative value,
when the received lighting-apparatus light amount is smaller than the predetermined value, the received lighting-apparatus light amount is not added to the corrected received-light amount, and
when the received-lighting-apparatus light amount is greater than or equal to the predetermined value, the received lighting-apparatus light amount is added to the corrected received-light amount.

14. The method according to claim 1, further comprising:
storing schedule information of a user including scheduled position information and scheduled time information; and
calculating solar radiation amount information corresponding to the scheduled position information and the scheduled time information.

15. A non-transitory computer readable medium storing a program causing a computer to execute the method according to claim 1.

16. A cumulative received-light amount estimation apparatus comprising:
a solar radiation amount obtainer that obtains solar radiation amount information corresponding to position information of a device and time information;
a received-light amount calculator that calculates a corrected received-light amount obtained by correcting an amount of light received by the device, based on a radio field reception intensity of a wireless signal that includes the position information, the amount of light received being indicated by the solar radiation amount information; and
a cumulative value calculator that calculates a cumulative value that includes the corrected received-light amount.

17. The cumulative received-light amount estimation apparatus according to claim 16, further comprising:
a display that displays the cumulative value calculated by the cumulative value calculator.

18. A health care system comprising:
the cumulative received-light amount estimation apparatus according to claim 16;
a managing computer that manages an amount of light which a user is exposed to, a health condition of the user, and a sleeping condition of the user, based on the cumulative value obtained from the cumulative received-light amount estimation apparatus; and
a lighting apparatus.

19. The health care system according to claim 18, wherein the managing computer controls at least one of brightness of light emitted by the lighting apparatus and a light emitting period of the lighting apparatus, based on the amount of light which the user is exposed to, on information indicating the health condition of the user, and on information indicating the sleeping condition of the user.

20. The health care system according to claim 19, wherein when an amount of light which the user has been exposed to in one day is less than a value that is previously set, the managing computer performs, for a following day, at least one of increasing the brightness of light emitted by the lighting apparatus and extending the light emitting period of the lighting apparatus.

* * * * *